(12) United States Patent
Kushiku et al.

(10) Patent No.: US 7,161,029 B2
(45) Date of Patent: Jan. 9, 2007

(54) DIL-LYSINE MONOSULFATE TRIHYDRATE CRYSTAL AND METHOD OF MAKING

(75) Inventors: Takeshi Kushiku, Kanagawa (JP); Dave Steckelberg, Eddyville, IA (US); Toshiya Tanabe, Eddyville, IA (US); Jirou Haga, Kanagawa (JP)

(73) Assignee: Ajinomoto Co., Inc., Tokyo (JP)

( * ) Notice: Subject to any disclaimer, the term of this patent is extended or adjusted under 35 U.S.C. 154(b) by 201 days.

(21) Appl. No.: 10/736,511

(22) Filed: Dec. 17, 2003

(65) Prior Publication Data

US 2005/0132947 A1   Jun. 23, 2005

(51) Int. Cl.
    *C30B 29/54*     (2006.01)
(52) U.S. Cl. .......................... 562/562; 117/68; 117/70; 117/925; 117/927
(58) Field of Classification Search ................ 562/562; 117/68, 70, 925, 927
    See application file for complete search history.

(56) References Cited

U.S. PATENT DOCUMENTS 4,256,917 A * 3/1981 Takayanagi et al. ........ 562/562
4,399,304 A    8/1983 Matsuishi et al. .......... 562/445
5,689,001 A    11/1997 Hasegawa et al. .......... 562/554
6,329,548 B1 * 12/2001 Hasegawa et al. .......... 562/562
6,617,444 B1   9/2003 Mori et al. .............. 536/26.22

OTHER PUBLICATIONS

Yamada, Yamamoto, and Chibata, Optical Resolution of DL-lysine by Preferential Crystallization Procedure, J. Agr. Food Chem., vol. 21, No. 5, 1973, pp. 889-894.*

Roth et al., "Biological Efficiency of L-Lysine Base and L-Lysine Sulphate Compared with L-Lysine HCl in Piglets"; Agribio.Res., 1994, vol. 47 No. 2, pp. 177-186.

Aketa, K. et al., "Stereochemical Studies. XL. A Biomimetic Conversion of L-Lysine into optically Active 2-Substituted Piperidines. Synthesis of D- and L-Pipecolic Acid, and (S) (+)-Coniine from L-Lysine"; Chem. Pharm. Bull., 1976, vol. 24, No. 4, pp. 621-631.

International Search Report for PCT Appl. No. PCT/JP2004/019465 (Apr. 26, 2005).

* cited by examiner

*Primary Examiner*—Robert Kunemund
*Assistant Examiner*—Maria Veronica Ewald
(74) *Attorney, Agent, or Firm*—Cermak & Kenealy, LLP; Shelly Guest Cermak

(57) ABSTRACT

A diL-lysine monosulfate trihydrate crystal which has a large tabular form and is more easily separable from the mother liquor. The crystal is obtained by a novel process of conducting crystallization at a lower temperature.

9 Claims, 8 Drawing Sheets

[Fig. 4] The relation between temperature and the solubility of di-L-lysine sulfate.

DIL-LYSINE MONOSULFATE TRIHYDRATE CRYSTAL AND METHOD OF MAKING

BACKGROUND OF THE INVENTION

1. Field of the Invention

The present invention relates to L-lysine sulfate crystals and methods for making the crystals, and more specifically to diL-lysine sulfate crystals with crystal water incorporated into the structure, and a method of making these crystals in larger quantities which are readily separable from the mother liquor. Finally, the present invention relates to products containing L-lysine made by the above novel method.

2. Brief Description of the Related Art

L-lysine is one of the essential amino acids and is widely used in the pharmaceutical and agricultural industries as a nutrition regulator and feed additive, among other uses. It circulates primarily as L-lysine hydrochloride (www.ajinomoto.co.jp/ajinomoto/A-life/aminoscience/siryou/lijin.html). When in the form of diL-lysine sulfate, feed effects equivalent to those of L-lysine hydrochloride are seen (Roth et al., 1994: Biological Efficiency of L-Lysine Base and L-Lysine Sulphate Compared with L-Lysine HCl in Piglets; Agribio. Res. 47(2):177–186 (1994)).

Crystals of diL-lysine sulfate are known to contain anhydrous diL-lysine sulfate (Aketa et al., Stereo chemical studies XL A biomimetic conversion of L-lysine into optically active 2-substituted; Chem. Pharm. Bull. 24(4):623–31 (1976)). Therefore, alcohol is often added to the diL-lysine sulfate aqueous solution to enable production of anhydrous diL-lysine sulfate crystals. Because the added alcohol must be removed from the resulting crystals, an extra purification step must be added to the process, further reducing the yield of crystals. See Aketa et al.

Anhydrous diL-lysine sulfate crystals are known to be highly soluble in water, which also contributes to the low yields of crystals. As a result, the high concentration of crystals in the mother liquor causes a decreased rate of crystallization. The small amounts of crystals that are eventually obtained are very fine and small, which causes a difficult separation from the mother liquor, further exacerbating the low yield problem.

Therefore, there is clearly a need in the art for improved methods of obtaining pure and highly separable L-lysine crystals. As L-lysine is such an important component in products for many different industries, highly efficient methods for crystallizing and purifying L-lysine are clearly needed in the art.

The present invention describes a novel method for crystallization and purification of L-lysine that is highly efficient, provides significantly increased yields, and results in easier and more efficient separation of the product crystals from the mother liquor. The present invention also describes a novel crystal form of L-lysine sulfate.

SUMMARY OF THE INVENTION

The present invention describes a technique for crystallizing diL-lysine monosulfate trihydrate, and the resulting crystals, which are superior for separability and high yields, among other superior qualities.

According to a first aspect of the invention, a method of producing a diL-lysine monosulfate trihydrate crystal from a solution is described, comprising mixing a lysine-based solution with sulfuric acid at a temperature of between approximately −10° C. and approximately 35° C., allowing crystals to form, and recovering the crystals.

According to another aspect of the present invention, a method of producing diL-lysine monosulfate is described, comprising mixing a lysine-based solution with sulfuric acid at a temperature of between approximately −10° C. and approximately 35° C., allowing crystals to form, recovering the crystals, and drying crystals to remove the crystal water, and collecting diL-lysine sulfate is described.

According to a further aspect of the present invention, a diL-lysine monosulfate trihydrate crystal is described which is characterized by having peaks at diffraction angles 2θ of 16.6° and 17.0° in powder X-ray diffraction.

According to an even further aspect of the present invention, a method of producing a diL-lysine monosulfate trihydrate crystal from an solution is described, comprising mixing a lysine-based solution with sulfuric acid at a temperature above approximately 40° C., and allowing crystals to form, then lowering the temperature until it is between approximately −10° C. and approximately 35° C., and allowing crystals to form, and recovering the crystals.

According to an even further aspect of the present invention, a diL-lysine monosulfate trihydrate crystal is described.

According to an even further aspect of the present invention, a diL-lysine monosulfate trihydrate crystal is described that is produced by the process described above.

According to an even further aspect of the present invention, a composition containing L-lysine, prepared by the above-described process, followed by a drying step.

Still other objects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to preferred embodiments of the invention, given only by way of example, and with reference to the accompanying figures, in which.

DESCRIPTION OF THE PREFERRED EMBODIMENTS

The present invention describes a novel crystallization technique and purification process, as well as novel crystals of L-lysine sulfate for use in any application in which L-lysine is currently used, such as feed additives or nutritional supplements. More specifically, the present invention describes the formation of novel diL-lysine monosulfate trihydrate crystals through a novel purification process. The present invention describes how varying, and particularly lowering, the crystallization temperature when conducting crystallization results in the precipitation of novel diL-lysine monosulfate trihydrate, in addition to the crystals of anhydrous diL-lysine sulfate.

The novel diL-lysine monosulfate trihydrate crystals are advantageous over anhydrous diL-lysine sulfate crystals because they are larger and more readily separable from the mother liquor. Furthermore, due to lower solubility in water, a higher crystallization yield results, and since diL-lysine monosulfate trihydrate crystals incorporate water into the crystals as crystal water, an improved crystallization yield can be anticipated due to a reduction in the quantity of solvent used in crystallization.

Figure 1:
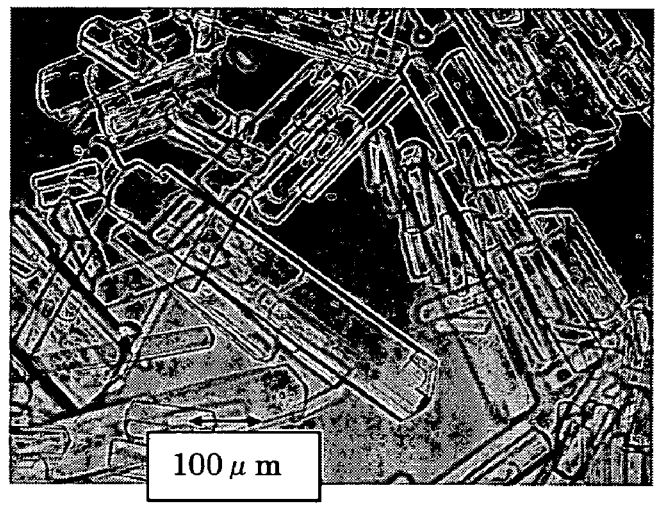
FIG. 1 illustrates crystals of diL-lysine monosulfate trihydrate.
Figure 2:
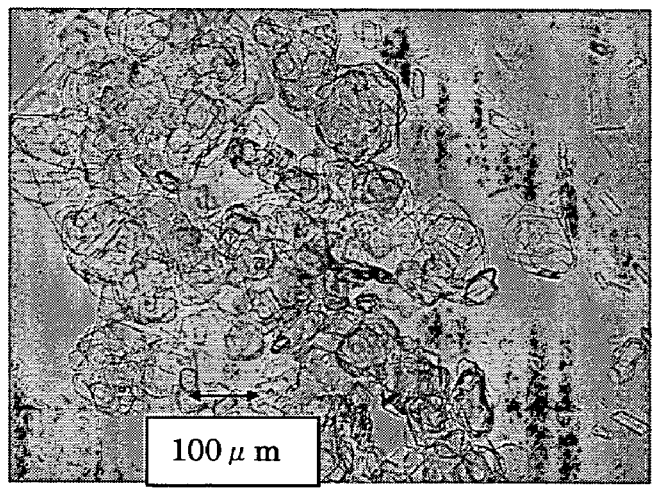
FIG. 2 illustrates crystals of anhydrous diL-lysine sulfate.

The diL-lysine monosulfate trihydrate crystals of the present invention have improved size and general form rendering them more easily separable from the mother liquor. FIG. 1 depicts the novel diL-lysine monosulfate trihydrate crystals, shown in the form of large tabular crystals. As shown in FIG. 1, these crystals are larger, tabular, and column-like. These larger crystals are more readily separable from the mother liquor during the separation step subsequent to crystallization. FIG. 2 shows, for comparison, the anhydrous diL-lysine sulfate crystals, which are clearly smaller and form in clumps, making them difficult to separate from the mother liquor, and causing lower yields.

The diL-lysine monosulfate trihydrate crystals of the present invention have water incorporated into the crystals, which enables their preferred form, size, and renders them more readily separable. Preferably, the crystals have 3 moles of water incorporated into the crystal lattice, resulting in a diL-lysine monosulfate trihydrate crystal.

The starting material for the novel crystallization method is in the form of a lysine-based solution, preferably a diL-lysine sulfate aqueous solution. Preferably, the solution is over-saturated with diL-lysine sulfate, which enables the beginning of crystallization to occur. The diL-lysine sulfate solution that serves as a starting material may be prepared by any method known to those of skill in the art. The preferred method of obtaining the starting solution is to cause accumulation of diL-lysine sulfate in a culture solution as a result of fermentation. Japanese Unexamined Patent Publication (KOKAI) Heisei No. 5-30985 and Heisei No. 5-244969 teach exemplary methods of accumulating diL-lysine sulfate in a culture solution by fermentation. The crystallization process can be started directly from this fermentation broth by evaporating, followed by cooling. Alternatively, another possible method of obtaining the starting solution includes obtaining diL-lysine and sulfuric acid from commercial sources and mixing them in an aqueous solution.

The concentration of the diL-lysine sulfate solution which serves as a starting material can be adjusted for crystallization by methods known in the art. Typically, the solution should be over-saturated. Methods for determining formulation of the starting solution, including parameters such as concentration, temperature, and solubility are known in the art. As a guideline, the concentration need only be greater than the solubility of the diL-lysine sulfate. In one embodiment, if the crystallization temperature is 20° C., the solubility of diL-lysine sulfate at his temperature is 102.9 g/100 g water. Thus, the concentration of the diL-lysine sulfate in the crystallization starting material solution would be adjusted to 102.9 g/100 g water or greater. Adjusting the concentration may be accomplished by known methods in the art, for example, by pressure reduction or evaporation. However, any known method for adjusting the concentration to achieve over-saturation may be used.

Figure 3:
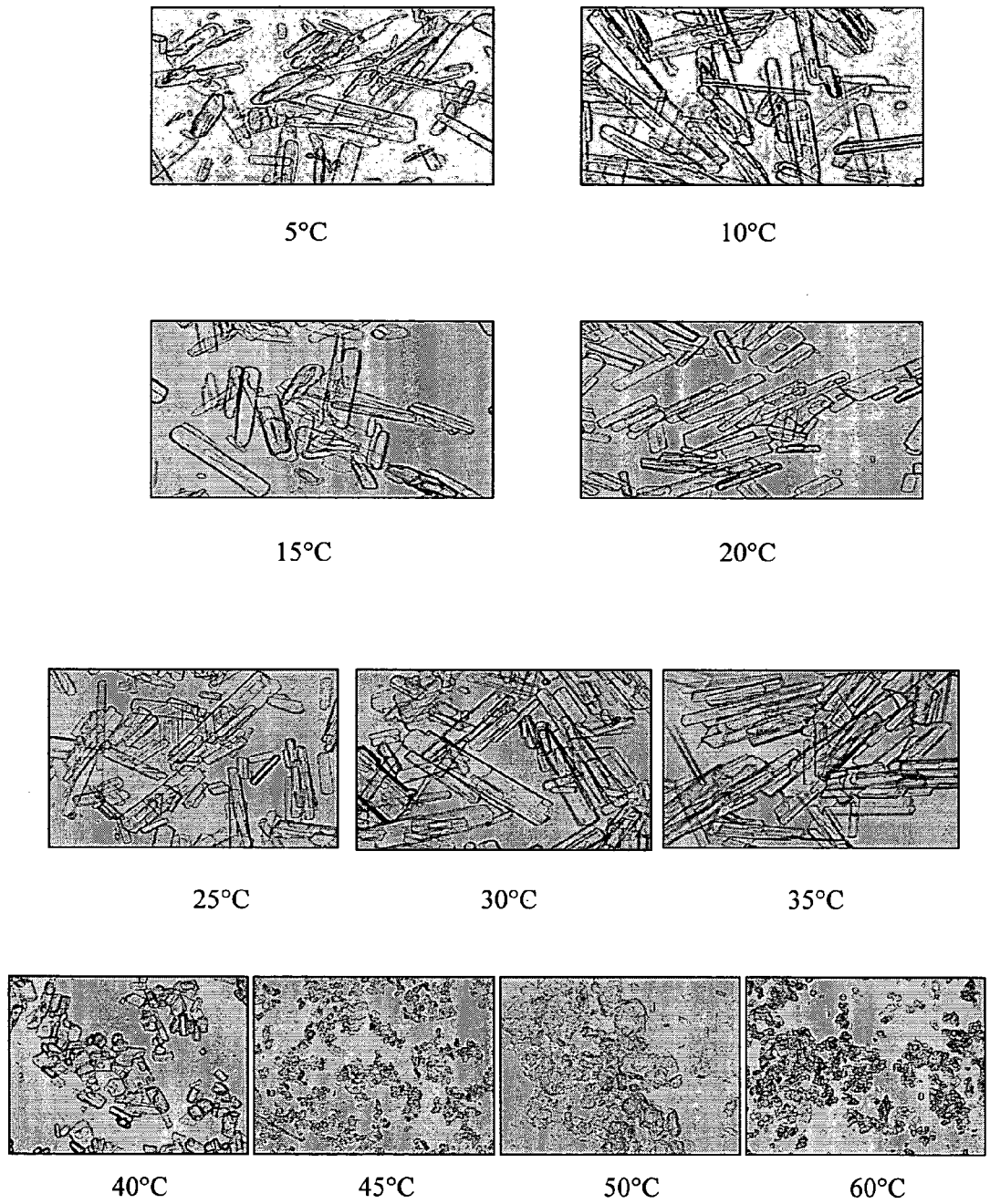
FIG. 3 illustrates crystals precipitated out of an aqueous solution of diL-lysine sulfate at various temperatures.

To obtain the larger, more readily separable diL-lysine monosulfate trihydrate crystals of the present invention, one may use the novel crystallization process of the present invention. The method of the present invention includes either beginning the crystallization at a temperature of between −10° C. and 35° C., or beginning at a higher temperature and subsequently lowering the temperature until it is in the above-desired range. These temperatures are approximate and may vary plus or minus 5° C. It was discovered that reducing the temperature of the starting material resulted in precipitation of the diL-lysine monosulfate trihydrate from the aqueous solution which results in the larger crystalline form. FIG. 3 depicts the form of the crystals when precipitated at varying temperatures from 5° C. to 60° C. at 5° C. intervals. As can be seen over the temperature range, the diL-lysine monosulfate trihydrate crystals which form below 35° C. are larger, more tabular and column-like. Over 40° C., the diL-lysine sulfate crystals which form are small and in clumps. Therefore, the method of the present invention includes a crystallization step in which the temperature is preferably equal to or lower than approximately 35° C., more preferably below approximately 30° C., and even more preferably below approximately 25° C., and even more preferably below approximately 20° C. Most preferably, the temperature for crystallization is approximately 10° C. To enable the process, seed crystals of diL-lysine monosulfate trihydrate may be added to the starting material solution.

Furthermore, in another embodiment, the crystals may be precipitated as anhydrous diL-lysine sulfate crystals at a temperature of 40° C. or greater, followed by lowering the temperature to 35° C. or below. In this way, diL-lysine monosulfate trihydrate crystals of the present invention are obtained through conversion into diL-lysine monosulfate trihydrate crystals. This method was advantageous in that the elimination of impurities through rearrangement was accomplished.

Following the crystallization step, the diL-lysine monosulfate trihydrate crystals are separated from the mother liquor by usual methods of separation, including but not limited to, suction filtration, centrifugal filtration, centrifugal separation, and press filtration. Following separation, the crystals can be dried by any of the usual methods known in the art and collected for use in industry.

Water Solubility of diL-Lysine Monosulfate Trihydrate

Figure 4:
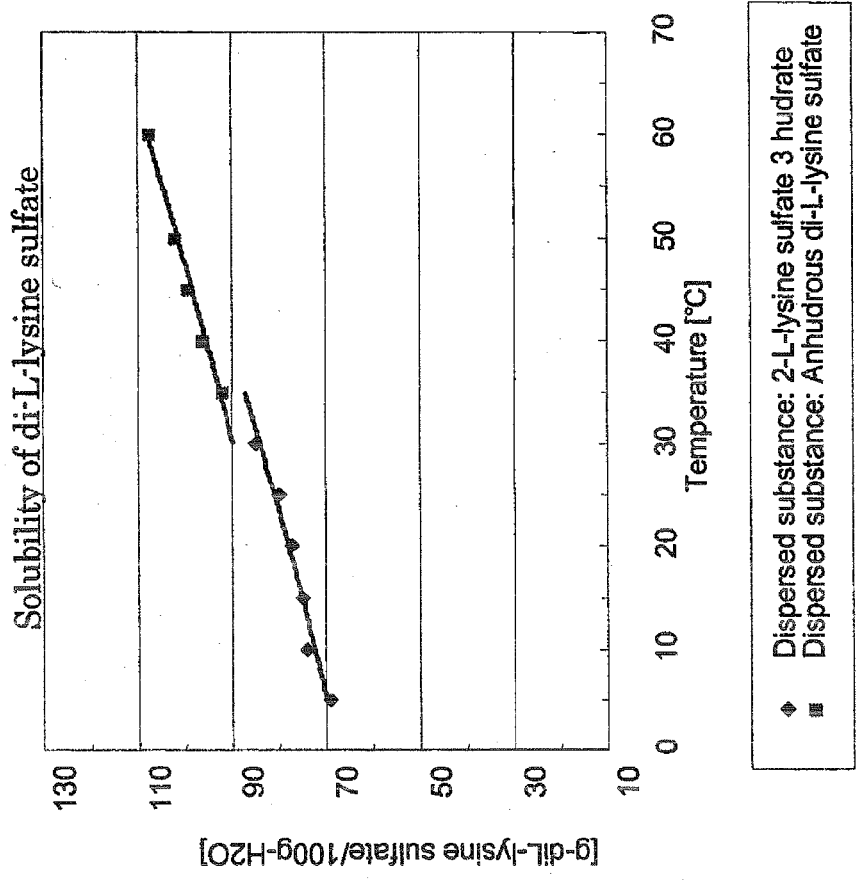
FIG. 4 is a graph showing the relationship between temperature and solubility of diL-lysine sulfate.

DiL-lysine monosulfate trihydrate precipitates at 35° C. and below and anhydrous diL-lysine sulfate precipitates at 40° C. and above. Normally, solubility in water tends to continuously drop as the temperature decreases. However, as shown in FIG. 4, the solubility curve of diL-lysine monosulfate trihydrate was surprisingly discontinuous with that of anhydrous diL-lysine sulfate. That is, over the temperature range at which diL-lysine monosulfate trihydrate precipitated, the degree of solubility was lower than the degree of solubility that would be anticipated from the solubility curve of anhydrous diL-lysine sulfate. Thus, crystals precipitating as diL-lysine monosulfate trihydrate were found to have a better crystallization yield than crystals precipitating as anhydrous diL-lysine sulfate. This is because for the diL-lysine monosulfate trihydrate crystals, the water itself is captured in the crystal lattice so that when crystallization proceeds, available free water in the supernatant decreases, therefore, there is less supernatant water to aid in dissolution of lysine sulfate. This contributes to the higher yield, that is more crystal precipitates.

Characteristics of diL-Lysine Monosulfate Trihydrate

Figure 5:
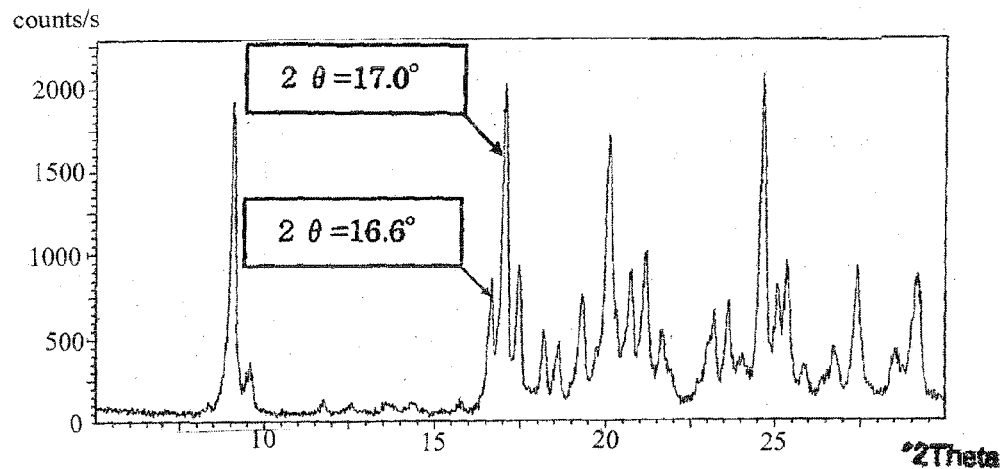
FIG. 5 shows the powder X-ray diffraction pattern of diL-lysine monosulfate trihydrate crystals.

Powder X-ray diffraction, thermal analysis, and L-lysine content analysis were conducted to further elucidate the characteristics of the diL-lysine monosulfate trihydrate crystals of the present invention. FIG. 5 shows the powder X-ray diffraction of diL-lysine monosulfate trihydrate crystals and FIG. 6 shows the powder X-ray diffraction of diL-lysine monosulfate trihydrate crystals.

Figure 6:
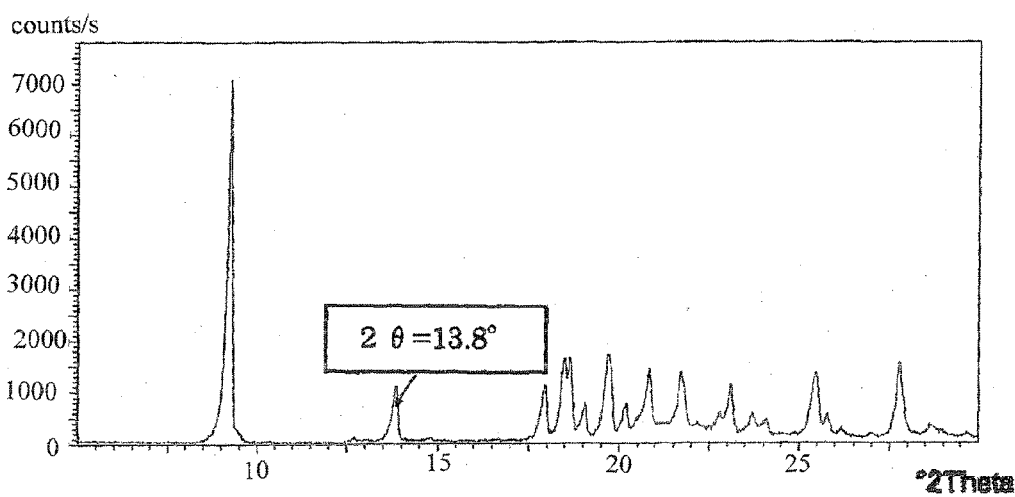
FIG. 6 shows the powder X-ray diffraction pattern of anhydrous diL-lysine sulfate crystals.

As shown in FIGS. 5 and 6, diL-lysine monosulfate trihydrate crystals exhibited diffraction peaks when the diffraction angle $2\theta=16.6°$ and $17.0°$. These diffraction peaks were not exhibited by the anhydrous diL-lysine sulfate crystals. Additionally, although anhydrous diL-lysine sulfate exhibited a diffraction peak at a diffraction angle of $2\theta=13.8°$, this diffraction peak was not exhibited by diL-lysine monosulfate trihydrate crystals. Since diL-lysine monosulfate trihydrate crystals and anhydrous diL-lysine sulfate crystals exhibit different powder X-ray diffraction patterns, the two were determined to have different crystalline forms.

Figure 7:
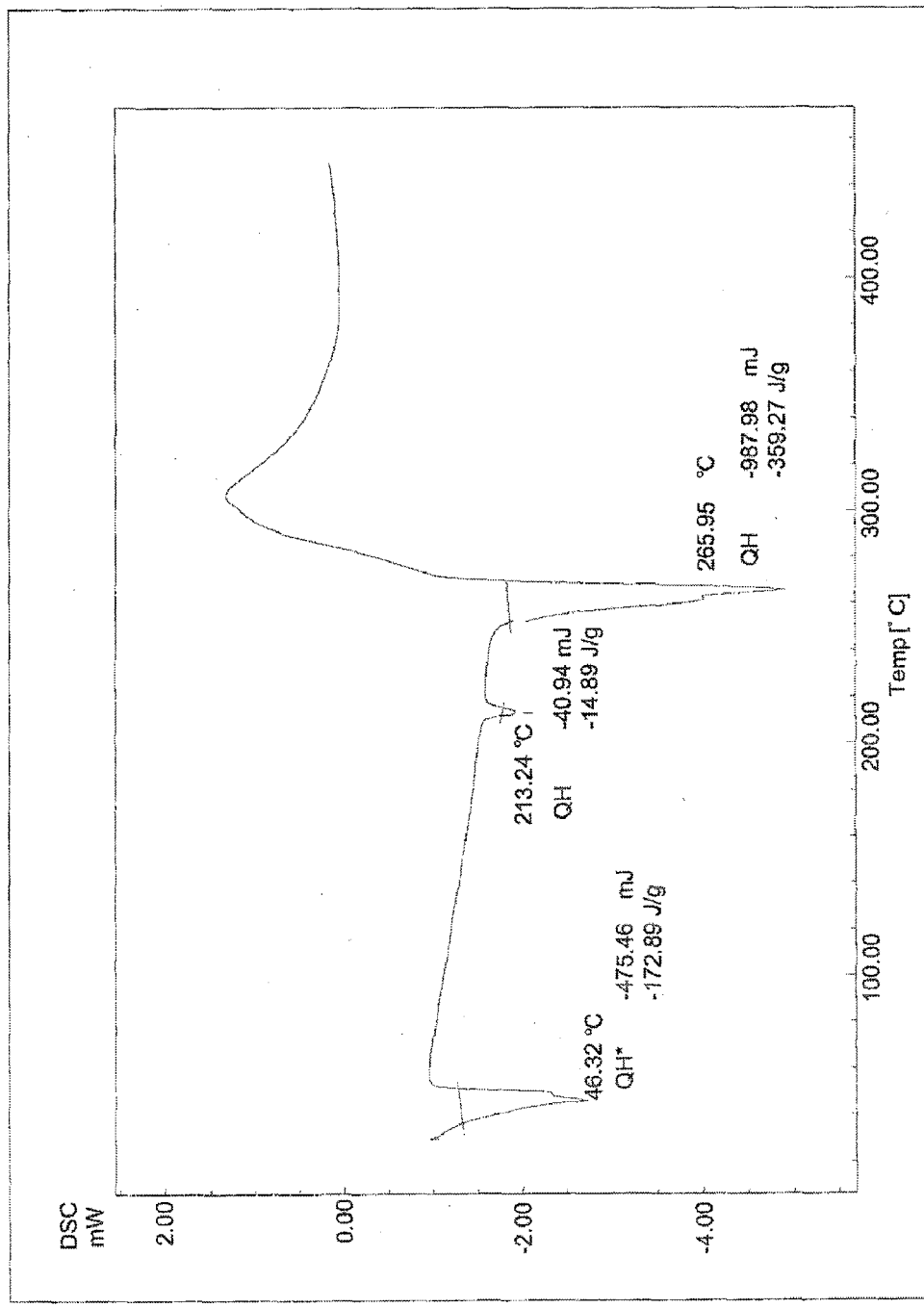
FIG. 7 shows the thermal analysis results for diL-lysine monosulfate trihydrate crystals.
Figure 8:
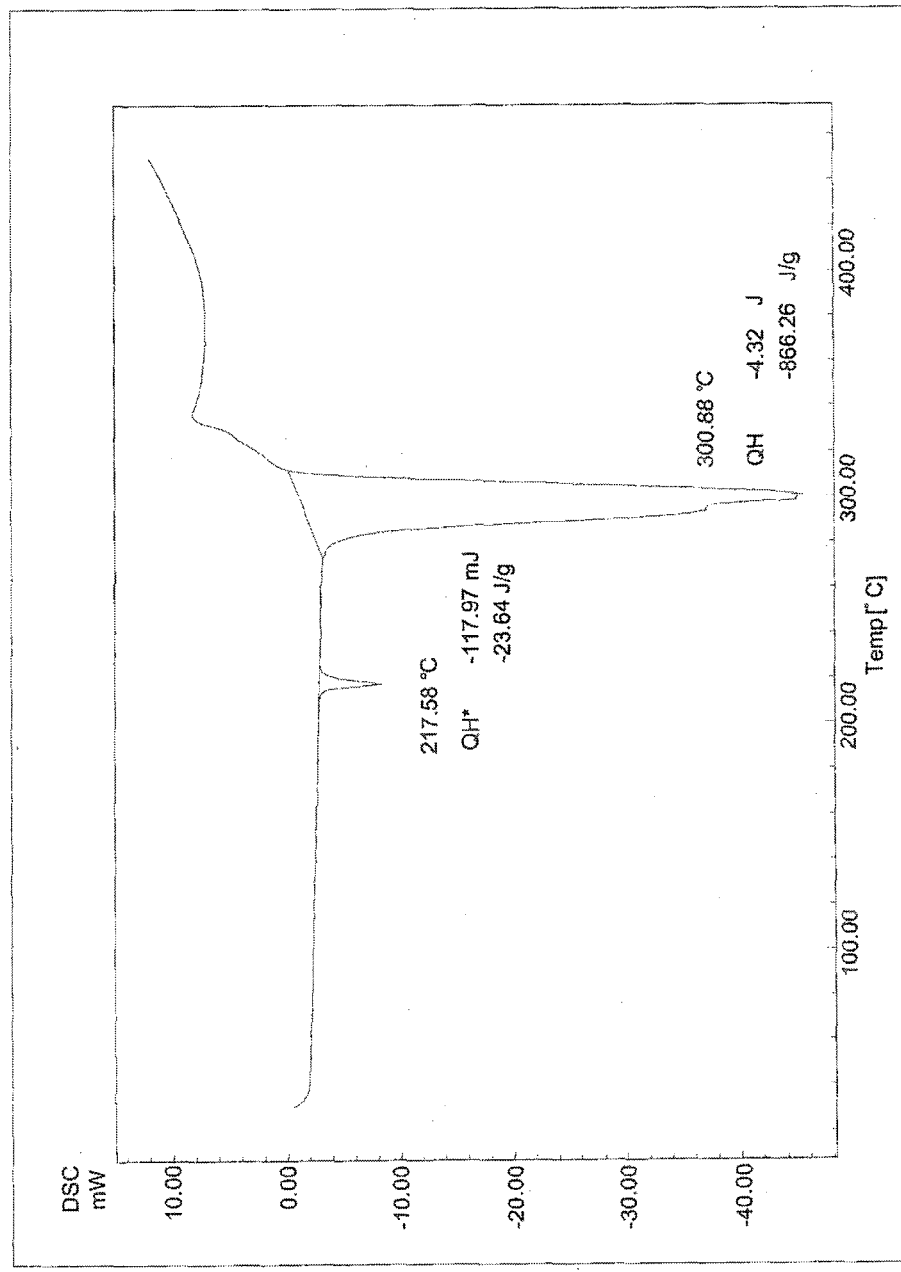
FIG. 8 shows the thermal analysis results for anhydrous diL-lysine sulfate.

Thermal analysis was conducted to further elucidate the properties of diL-lysine monosulfate trihydrate crystals. FIG. 7 shows the thermal analysis results for diL-lysine monosulfate trihydrate crystals and FIG. 8 shows the thermal analysis results for anhydrous diL-lysine sulfate crystals. Comparing FIGS. 7 and 8, the two crystals both exhibited heat absorption peaks in the vicinity of 215° C. and 300° C. This was attributed to melting of diL-lysine sulfate or heat absorption accompanying decomposition.

A heat absorption peak was uniquely observed in diL-lysine monosulfate trihydrate at 46° C. This was presumed to be the heat absorption peak occurring as diL-lysine monosulfate trihydrate crystals lost their water. Since diL-lysine monosulfate trihydrate loses its water at an extremely low temperature in this manner, diL-lysine monosulfate trihydrate crystals readily lose their crystal water during the drying step, which is extremely advantageous to the industrial production of anhydrous diL-lysine sulfate.

The L-lysine content of the diL-lysine monosulfate trihydrate crystals obtained by the method of example 1 is preferably around 65%. L-lysine can be measured by any method known to those in the art, including HPLC. More preferably, the L-lysine content can be increased to greater than 75% by converting the crystals to an anhydrous state by eliminating the crystal water at approximately 46° C. Japanese Unexamined Patent Publication (KOKAI) Heisei No. 5-192089 provides examples of substances commonly containing diL-lysine sulfate obtained by directly drying the fermentation broth, and therefore, employing no purification step. Crystals obtained by this method typically contain below 50% L-lysine. Therefore, by comparison, the crystals of the present invention are superior in that they contain a higher L-lysine content.

The present invention will be more concretely explained below with reference to following Examples, which are intended to be illustrative only and are not intended to limit the scope of the invention as defined by the appended claims.

EXAMPLES

The data disclosed herein were obtained by analysis under the following conditions:
a. L-lysine content: Hitachi Amino Acid Analyzer L-8800 (protein hydrolysis product analysis method)
b. Powder X-ray diffraction: Phillips X'Pert TYPE PW3040/00
c. Thermal analysis: Shimadsu Seisakujo differential Scanning Calorimeter DSC-60
d. Elemental Analysis: Analysis of carbon, hydrogen, and nitrogen was by elemental analyzer vario EL3 (elemental); analysis of oxygen was by organic element analyzer CHN-O-Rapid (elemental); analysis of sulfer was by Ion chlomato analyzer (sulfer was analyzed as sulfuric acid, which is generated by combustion with oxygen); all analyses conducted by Tore Research Center Example 1

A 584 g quantity of 50% L-lysine solution obtained from a commercial source (Daiichi Fine Chemicals, Ltd., lot A2882) was placed in a 500 ml glass beaker and maintained at 10° C. in a water bath. A 102 g quantity of 98% sulfuric acid (reagent grade, Junsei Kagaku lot 1L8102) was then added and the L-lysine was converted to diL-lysine sulfate. As a result, large columnar crystals precipitated, as shown in FIG. 1.

The slurry obtained was stirred and aged overnight at 5° C., after which the mother liquid and crystals were separated by suction filtration using filter paper.

Figure 9:
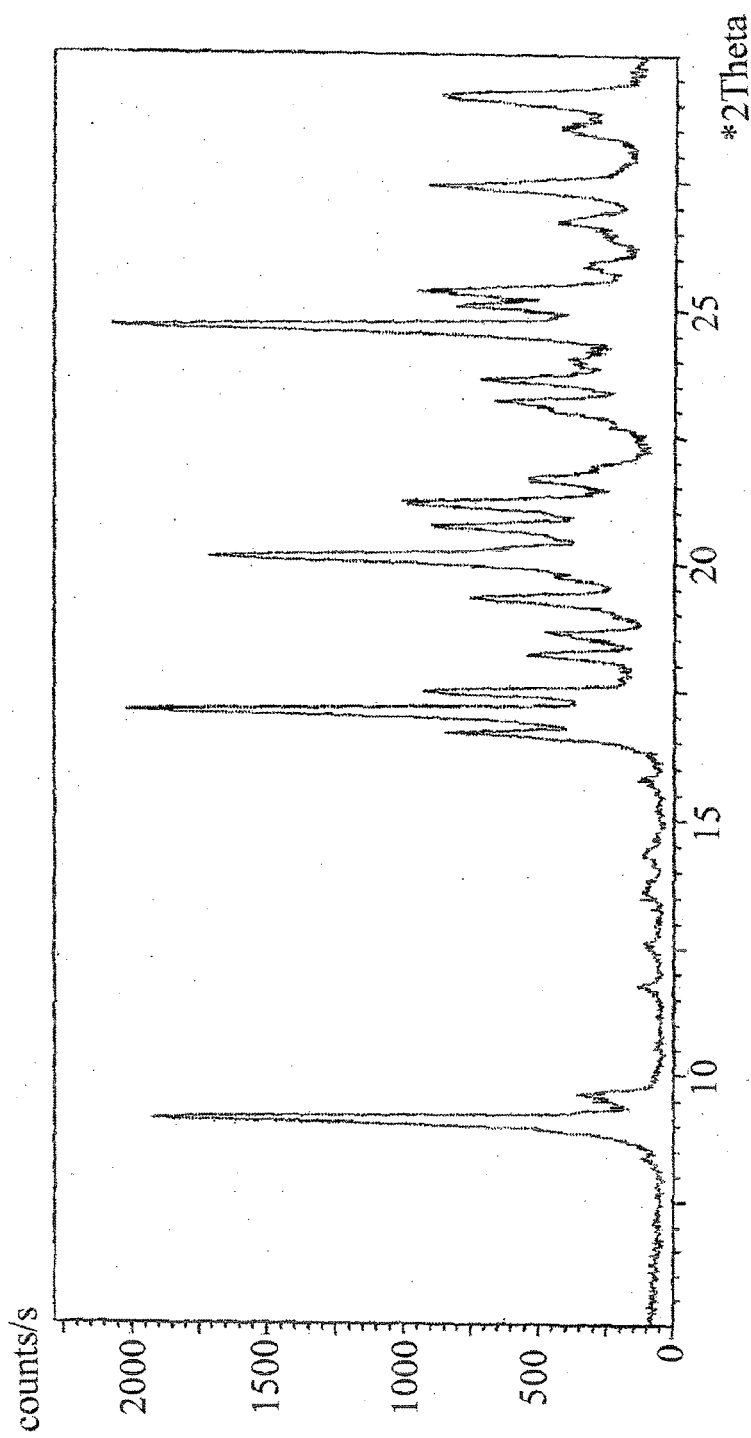
FIG. 9 shows the powder X-ray diffraction pattern of crystals obtained in Example 1.

Table 1 shows the results of elemental analysis. FIG. 9 shows the powder X-ray diffraction chart.

|  | Example 1 | Theoretical values of diL-lysine monosulfate trihydrate crystal $2(C_6H_{16}N_2O_2)\cdot SO_4\cdot 3H_2O$ |
|---|---|---|
| Carbon | 32.38% | 32.3% |
| Hydrogen | 8.16% | 8.5 |
| Nitrogen | 12.42% | 12.6 |
| Oxygen | 38.25% | 39.5 |
| Sulfur | 7.34% | 7.2 |

As shown in Table 1, the elemental analysis results of the crystals obtained in Example 1 approximated the theoretical elemental composition of diL-lysine monosulfate trihydrate. Accordingly, the crystals obtained in Example 1 were determined to be diL-lysine monosulfate trihydrate.

As shown in FIG. 9, the crystals obtained in Example 1 exhibited diffraction peaks at diffraction angles $2\theta=16.6°$ and $17.0°$, and did not exhibit a diffraction peak at $13.6°$. Thus, they were determined to be diL-lysine monosulfate trihydrate.

Example 2

For comparison purposes, diL-lysine sulfate crystallization was conducted by the same method as in Example 1 with the exception that the crystallization temperature was 45° C. A powder X-ray pattern was immediately obtained for the crystals obtained by separation from the mother liquor. The separated crystals were also dried at 105° C. and subjected to elemental analysis.

Figure 10:
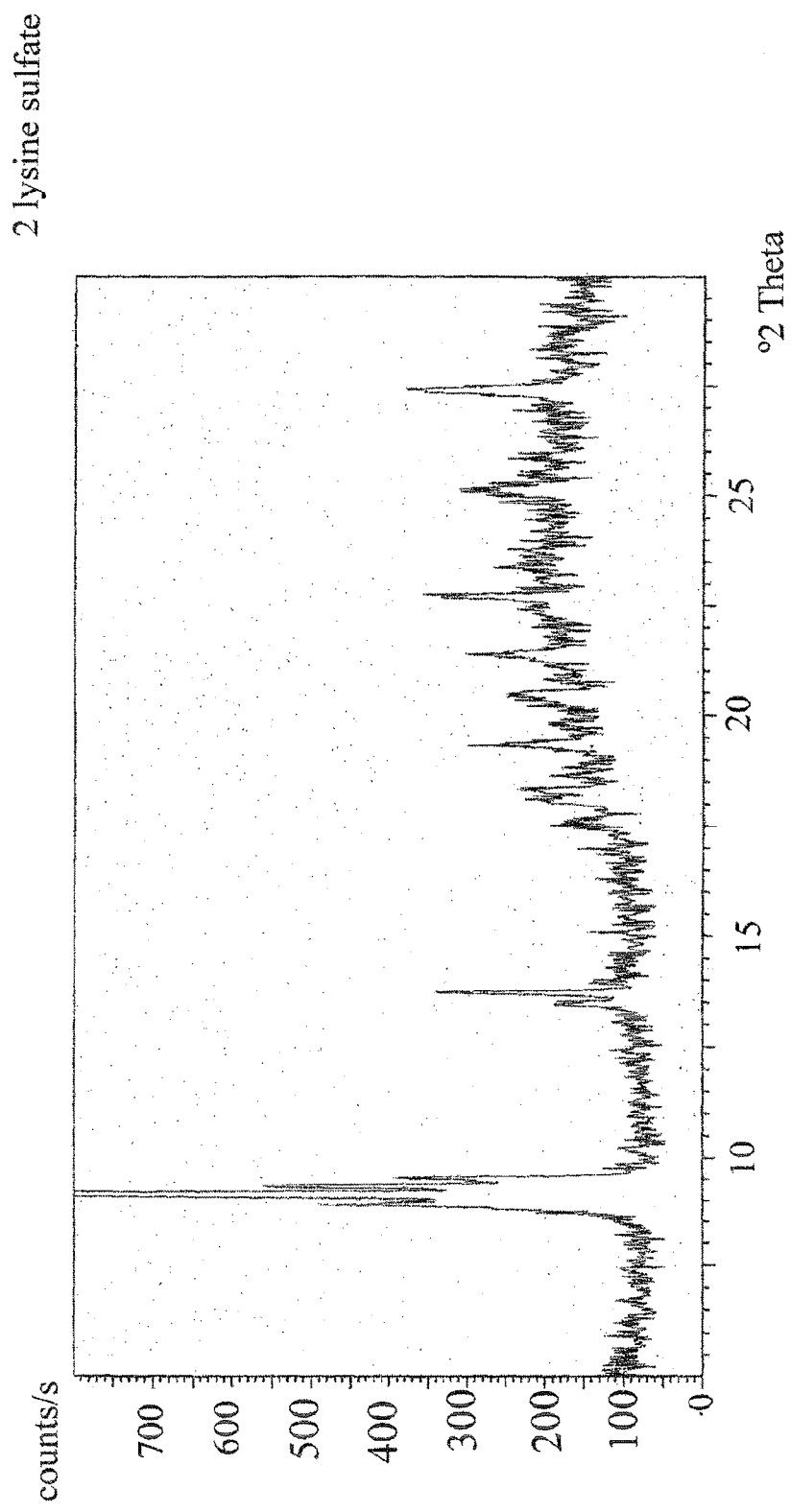
FIG. 10 shows the powder X-ray diffraction pattern of crystals obtained in Example 2.

FIG. 10 shows the powder X-ray pattern. Table 2 shows the results of elemental analysis.

|  | Example 2 | Theoretical values of anhydrous diL-lysine sulfate crystal $2(C_6H_{16}N_2O_2) \cdot SO_4$ |
|---|---|---|
| Carbon | 36.76% | 36.7% |
| Hydrogen | 7.75% | 8.2% |
| Nitrogen | 14.12% | 14.3% |
| Oxygen | 31.91% | 32.7% |
| Sulfur | 8.32% | 8.2% |

As shown in Table 2, the analytic values of the crystals obtained in Example 2 approximated the theoretical values of anhydrous diL-lysine sulfate crystals. Accordingly, the crystals obtained in Example 2 were determined to be anhydrous diL-lysine sulfate.

As shown in FIG. 10, the anhydrous diL-lysine sulfate crystals exhibited a unique diffraction peak at a diffraction angle of $2\theta=13.8°$. Further, the $2\theta=16.6°$ and $17.0°$ peaks unique to diL-lysine monosulfate trihydrate crystals were not observed. Accordingly, the crystals obtained in Example 2 were determined to be anhydrous diL-lysine sulfate.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

What is claimed is:

1. A diL-lysine monosulfate trihydrate crystal characterized by having peaks at diffraction angles 2θ of 16.6° and 17.0° as measured by powder X-ray diffraction.

2. The diL-lysine monosulfate trihydrate crystal of claim 1, produced by the process:
   a) mixing a lysine-based solution with sulfuric acid at a temperature of between approximately −10° C. and approximately 35° C., and allowing said crystal to form,
   b) recovering said diL-lysine monosulfate trihydrate crystal.

3. The diL-lysine monosulfate trihydrate crystal of claim 2, wherein said temperature is between approximately 0° C. and approximately 20° C.

4. The diL-lysine monosulfate trihydrate crystal of claim 3, wherein said temperature is approximately 10° C.

5. The diL-lysine monosulfate trihydrate crystal claim 2, wherein said crystal is recovered by filtration.

6. The diL-lysine monosulfate trihydrate crystal of claim 3, wherein said filtration is selected from the group consisting of suction filtration, centrifugal filtration, centrifugal separation, and press filtration.

7. A composition comprising diL-lysine sulfate, wherein said diL-lysine sulfate is prepared by the method of,
   a) mixing a lysine-based solution with sulfuric acid at a temperature of between approximately −10° C. and approximately 35° C., and allowing crystals to form which are characterized by having peaks at diffraction angles 2θ of 16.6° and 17.0° as measured by powder X-ray diffraction,
   b) recovering said crystals, and
   c) drying said crystals.

8. The composition comprising diL-lysine sulfate of claim 7, wherein the method for preparing the diL-lysine sulfate further comprises the step of collecting said diL-lysine sulfate.

9. A composition comprising a diL-lysine monosulfate trihydrate crystal, wherein diL-lysine monosulfate trihydrate crystal is prepared by the method of
   a) mixing a lysine-based solution with sulfuric acid at a temperature above approximately 40° C., and allowing crystals to form characterized by having peaks at diffraction angles 2θ of 16.6° and 17.0° as measured by powder X-ray diffraction,
   b) lowering the temperature until it is between approximately −10° C. and approximately 35° C., and allowing crystals to form,
   c) recovering said diL-lysine monosulfate trihydrate crystal, and
   d) drying said diL-lysine monosulfate trihydrate crystal.

* * * * *